US008858498B2

(12) United States Patent
West

(10) Patent No.: US 8,858,498 B2
(45) Date of Patent: Oct. 14, 2014

(54) NEEDLE ASSEMBLY WITH NEEDLE INJECTION DEPTH ADJUSTMENT

(75) Inventor: Robert E. West, Basking Ridge, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/698,686

(22) PCT Filed: May 17, 2010

(86) PCT No.: PCT/US2010/035072
§ 371 (c)(1),
(2), (4) Date: Nov. 19, 2012

(87) PCT Pub. No.: WO2011/146042
PCT Pub. Date: Nov. 24, 2011

(65) Prior Publication Data
US 2013/0066271 A1 Mar. 14, 2013

(51) Int. Cl.
*A61M 5/00* (2006.01)
*A61M 5/46* (2006.01)
*A61M 5/32* (2006.01)

(52) U.S. Cl.
CPC ............... *A61M 5/46* (2013.01); *A61M 5/3257* (2013.01); *A61M 5/3271* (2013.01)
USPC ....................................................... 604/117

(58) Field of Classification Search
USPC ........................................................ 604/117
See application file for complete search history.

(56) References Cited

U.S. PATENT DOCUMENTS 6,213,977 B1 * 4/2001 Hjertman et al. ............. 604/117
6,702,784 B1 3/2004 Sheckler et al.
(Continued)

FOREIGN PATENT DOCUMENTS

| GB | 1133555 A | * | 11/1968 |
| WO | 9501198 A1 | | 1/1995 |
| WO | 2010019936 A1 | | 2/2010 |
| WO | 2010053570 A1 | | 5/2010 |

*Primary Examiner* — Nicholas Lucchesi
*Assistant Examiner* — Diva K Chander
(74) *Attorney, Agent, or Firm* — Hoffmann & Baron, LLP

(57) ABSTRACT

In one aspect, a needle assembly is provided herein which includes a hub; a needle fixed to the hub, the needle having a proximal end and a distal end, the distal end formed for insertion into a patient; and, a body disposed on the hub so as to be moveable relative thereto, the body having a distal end with an aperture formed therein configured to permit passage therethrough of the needle. The body is releasably retainable in a first position on the hub where the distal end of the needle extends distally a first distance from the distal end of the body. Also, the body is retainable in a second position on the hub where the distal end of the needle extends distally a second distance from the distal end of the body, the second distance being less than the first distance. The hub is displaceable proximally relative to the body to urge the body from the first position to the second position. Advantageously, with the subject invention, a needle assembly is provided which may provide a stop for a needle injection to a first depth, with the stop being adjustable to permit the injection to be conducted at a shallower, second depth.

10 Claims, 3 Drawing Sheets

(56) References Cited

U.S. PATENT DOCUMENTS

| | | | |
|---|---|---|---|
| 7,670,314 B2* | 3/2010 | Wall et al. | 604/135 |
| 2004/0111064 A1 | 6/2004 | Asbaghi | |
| 2005/0203459 A1 | 9/2005 | Alchas | |
| 2005/0209568 A1 | 9/2005 | Stanley | |
| 2007/0005017 A1* | 1/2007 | Alchas et al. | 604/117 |
| 2009/0270806 A1* | 10/2009 | Macaulay et al. | 604/117 |

* cited by examiner

NEEDLE ASSEMBLY WITH NEEDLE INJECTION DEPTH ADJUSTMENT

FIELD OF THE INVENTION

This invention is directed to needle assemblies and, more particularly, to needle assemblies for permitting depth adjustment for injection.

BACKGROUND OF THE INVENTION

Medical injections of different depths, such as subcutaneous and intradermal injections, are known in the art. It is also known in the prior art to utilize a hard stop provided about a needle to ensure proper depth during injection.

In addition, sealing may be of concern during certain injections, particularly with shallow injections, such as intradermal injections. It has been found that a blister or wheal may form in the skin in which injected fluid collects as a pocket. Built-up pressure may cause the injected fluid to seep out the injection passage during or after injection.

SUMMARY OF THE INVENTION

In one aspect, a needle assembly is provided herein which includes a hub; a needle fixed to the hub, the needle having a proximal end and a distal end, the distal end formed for insertion into a patient; and, a body disposed on the hub so as to be moveable relative thereto, the body having a distal end with an aperture formed therein configured to permit passage therethrough of the needle. The body is releasably retainable in different positions on the hub where the needle extends distally different distances from the body. Advantageously, with the subject invention, a needle assembly is provided which may provide a stop for a needle injection to a first depth, with the stop being adjustable to permit the injection to be conducted at a shallower, second depth.

In a further aspect, the subject invention provides a needle assembly having a hub; a needle fixed to the hub, the needle having a proximal end and a distal end, the distal end formed for insertion into a patient; a body disposed on the hub so as to be moveable relative thereto, the body having a distal end with an aperture formed therein configured to permit passage therethrough of the needle; and, a pressure sensitive adhesive disposed on the distal end of the body. The body is releasably retainable in a first position on the hub where the distal end of the needle extends distally a first distance from the distal end of the body. Also, the body is retainable in a second position on the hub where the distal end of the needle extends distally from the distal end of the body less than the first distance from the distal end of the body, or is located proximally of the distal end of the body. The adhesive is configured to provide sufficient adherence to a patient's skin during an injection such that the body remains relatively fixed to the patient's skin to permit proximal movement of the hub relative to the body with the body being moved from the first position to the second position.

As used herein, the term "distal", and derivatives thereof, shall refer to a direction towards a patient during use, and the term "proximal", and derivatives thereof, shall refer to a direction away from a patient during use.

These and other features of the invention will be better understood through a study of the following detailed description and accompanying drawings.

DETAILED DESCRIPTION OF THE INVENTION

Figure 1:
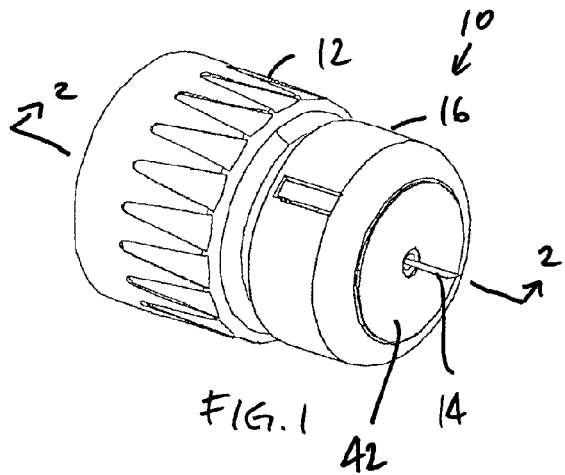
FIG. 1 is a front perspective view of a needle assembly formed in accordance with the subject invention.

With reference to the Figures, a needle assembly 10 is provided which is formed to provide depth adjustment for medical injections. The needle assembly 10 may be utilized with various injectors, but is particularly well-suited for use with pen injectors.

The needle assembly 10 generally includes a hub 12, a needle 14 fixed to the hub 12, and a body 16 disposed on the hub 12 so as to be moveable relative thereto. The body 16 acts as a stop and limits the permissible depth of injection of the needle 14 into a patient, as described below.

The hub 12 includes a tubular portion 18 and a transverse bulkhead 20 to which the needle 14 is attached in any known manner, such as with adhesion. Preferably, the tubular portion 18 includes a reduced-diameter neck portion 22 at its proximal end. The bulkhead 20 may span across the interior of the tubular portion 18, particularly at the neck portion 22.

Mounting features 24 are provided on the tubular portion 18, either interiorly and/or exteriorly thereof, formed to mount the needle assembly 10 onto a medical injector. The mounting features 24 may include a Luer surface and/or threads, or other known mounting features. Preferably, the hub 12 is formed of a material, e.g., thermoplastic material, which can withstand autoclaving or other forms of sterilization.

The needle 14 may be of any known type and includes a proximal end 26 and a distal end 28 formed for insertion into a patient. The distal end 28 may be sharpened. In addition, the proximal end 26 may be sharpened and may be formed with sufficient length to extend through a septum, or other closure, provided on a medical injector with the needle assembly 10 being mounted thereto.

The body 16 includes a distal end 30 from which extends proximally a skirt 32. Preferably, the skirt 32 is annular shaped and perimetrically bounds the distal end 30. The skirt 32 is sized and shaped to telescope over the neck portion 22 of the hub 12. An aperture 34 is formed in the distal end 30 of the body 16 configured to permit passage therethrough of the needle 14. The body 16 is preferably formed of a material, e.g., thermoplastic material, which can withstand autoclaving or other forms of sterilization.

The body 16 is disposed on the hub 12 so as to be movable relative thereto. Relative movement between the body 16 and the hub 12 can be achieved by telescoping movement of the skirt 32 about the neck portion 22. The hub 12 and the skirt 32 may be formed so that sufficient interengagement is generated therebetween to provide retentive force for maintaining the skirt 32 on the hub 12.

Figure 5:
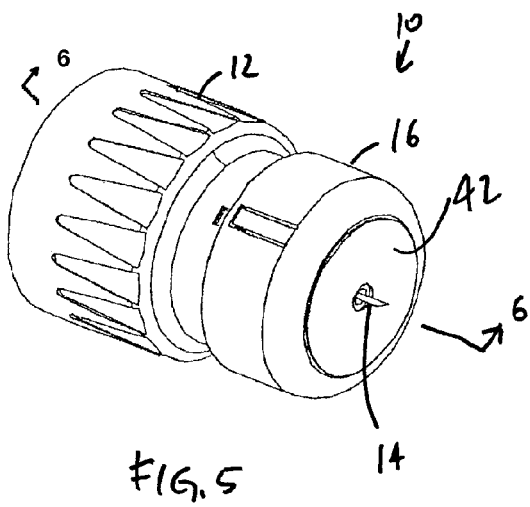
FIG. 5 shows the same needle assembly of FIG. 1, but in a second position.
Figure 6:
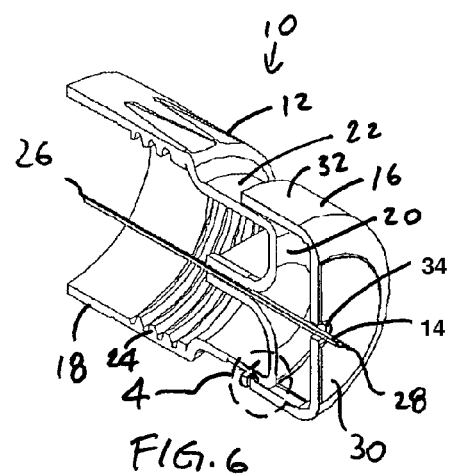
FIG. 6 is a cross-sectional view taken along line 6-6 of FIG. 5.
Figure 7:
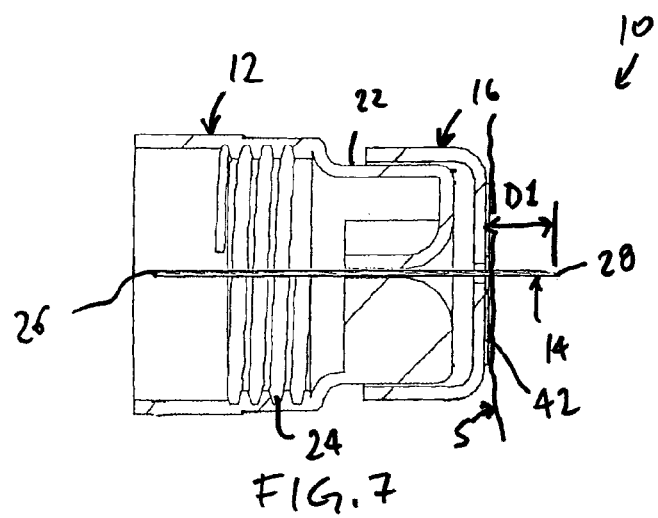
FIGS. 7 and 8 show first and second positions of a needle assembly formed in accordance with the subject invention.

With reference to FIGS. 1-8, it is preferred that the needle assembly 10 be utilized such that the body 16, particularly the distal end 30, acts as a hard stop in limiting the depth of an initial injection of the needle 14 into a patient. Specifically, with reference to FIGS. 1, 2 and 7, a first position of the body 16 is shown, where, the distal end 28 of the needle 14 extends a first distance D1 from the distal end 30 of the body 16 (FIG. 7). It is preferred that the body 16 be retained in the first position relative to the hub 12 so as to act as a hard stop against excessive insertion of the needle 14 into a patient. It is preferred that the body 16 be releasably retained in the first position so as to permit subsequent movement therefrom.

Figure 2:
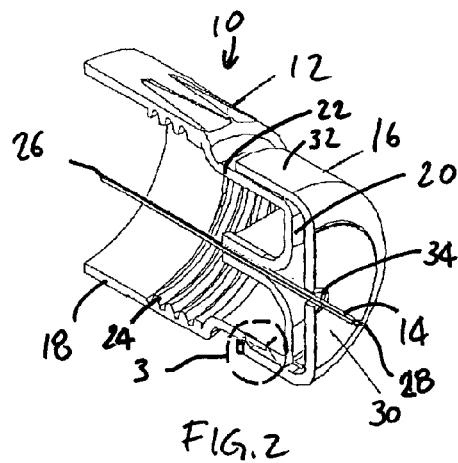
FIG. 2 is a cross-sectional view taken along line 2-2 of FIG. 1.
Figure 3:
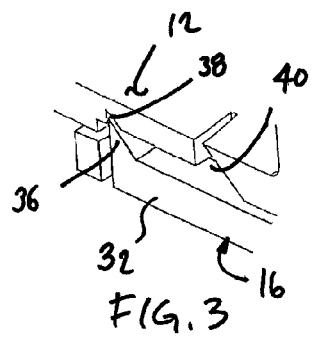
FIG. 3 is an enlarged section of Section 3 of FIG. 2.

By way of non-limiting example, and with reference to FIGS. 2 and 3, a releasable retaining arrangement may be provided including one or more retaining teeth 36 preferably formed on the body 16. A cooperating first retention slot 38 is preferably formed on the hub 12. The retaining teeth 36 are formed to be nestingly received in the first retention slot 38 in a limited snap engagement formation. The first retention slot 38 is formed of limited depth such that the retaining teeth 36 may be released from snap engagement with the first retention slot 38 and urged therefrom under sufficient separating force. Preferably, the separating force is generated by causing proximal movement of the hub 12 relative to the body 16.

Figure 8:
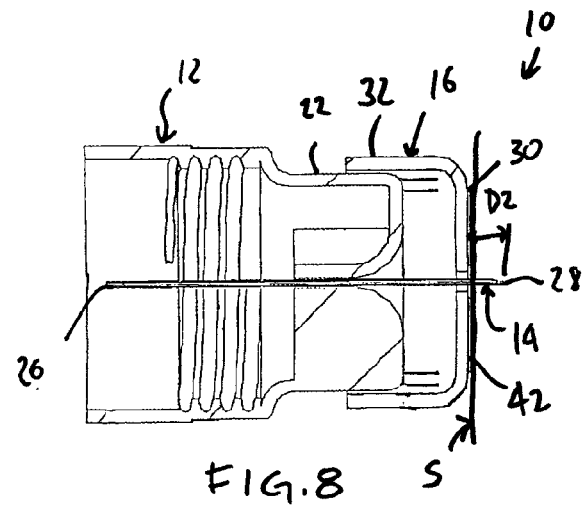
Figure 9:
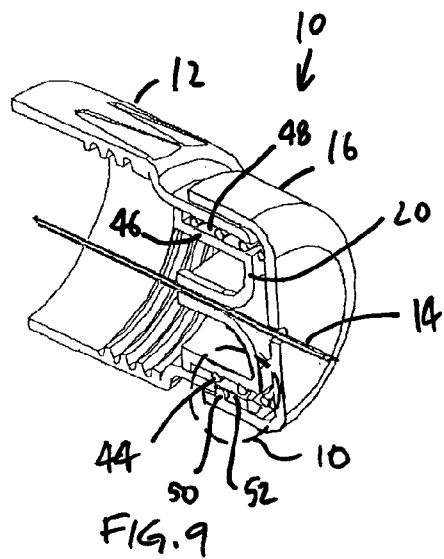
FIG. 9 is a cross-sectional view of a variation of a needle assembly formed in accordance with the subject invention.
Figure 10:
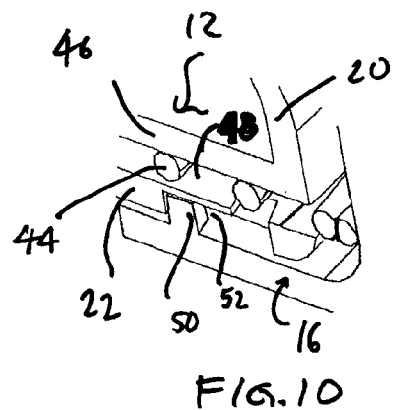
FIG. 10 is an enlarged section of Section 10 of FIG. 9.

A second retention slot 40, preferably formed on the hub 12, may be formed proximally from the first retention slot 38. The second retention slot 40 corresponds to a second position of the body 16 relative to the hub 12 where, as shown in FIGS. 5, 6 and 8, the distal end 26 of the needle 14 extends a distance D2 from the distal end 30 of the body 16. The distance D2 is less than the distance D1. In this manner, the needle 14 may be initially inserted to a first depth in a patient with the body 16 being in the first position and, with the hub 12 being subsequently moved proximally relative to the body 16, the body 16 may be urged to the second position from the first position.

Figure 4:
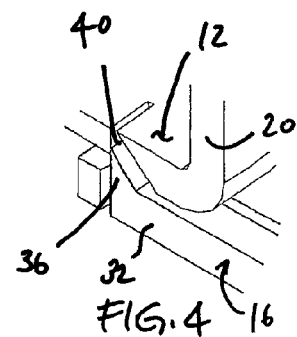
FIG. 4 is an enlarged section of Section 4 of FIG. 6.

The body 16 may be fixedly retained in the second position on the hub 12. To provide fixed retention, as shown in FIGS. 3 and 4, the second retention slot 40 may be formed with greater depth than the first retention slot 38 so as to cause the retaining teeth 36 to be fixedly retained therein, thus inhibiting further relative movement of the hub 12 relative to the body 16. More particularly, the second retention slot 40 may be formed with sufficient depth to prevent release from snap engagement with the retaining teeth 36. Alternatively, as discussed below, the body 16 may be releasably retained in the second position on the hub 12. Here, the second retention slot 40 may be formed in the same manner as the first retention slot 38 (e.g., same depth) so as to be configured to permit release by the retaining teeth 36 from snap engagement therewith. As will be appreciated by those skilled in the art, the retaining teeth 36, the first retention slot 38, the second retention slot 40 and/or any further retention slot may be partially or wholly formed on the hub 12 and/or the body 16 to operate in the same manner as described herein.

The first and second positions may be configured to correspond to particular injection depths for the needle 14. For example, the first position may correspond to a subcutaneous injection, while the second position may correspond to an intradermal injection. In addition, the first position may correspond to an intramuscular injection, while the second position may correspond to an intradermal injection, and likewise depending on the selected distances, any combination of depths may be employed thereby targeting two separate tissue compartments. In this manner, the needle 14 may be injected to a first depth, then withdrawn to a shallower depth for drug administration. By causing an initial deeper injection (at the distance D1), better sealing may be achieved about the needle 14 during the course of the drug administration at the shallower injection (at the distance D2) corresponding to the second position of the body 16 on the hub 12.

During use, it is preferred that the needle 14 be inserted into a patient with the body 16 being in the first position (FIG. 7). The distal end 30 of the body 16 acts as a hard stop to limit the depth of the insertion of the needle 14 into a patient's skin S. Thereafter, and prior to actuation of the injector to cause drug administration, the body 16 is maintained against the patient's skin S and the hub 12 is caused to move proximally relative to the body 16 so as to urge the body 16 into the second position (FIG. 8). Proximal movement of the hub 12 may be achieved by manual action, e.g., by holding the body 16 in one hand against the patient's skin and causing proximal movement of the hub 12 relative to the body 16, with the second hand (e.g., causing withdrawal of the hub 12 away from the patient's skin S). Actuation of the medical injector, and, thus, drug administration, may be caused with the body 16 in the second position.

Various modes of causing proximal movement of the hub 12 relative to the body 16 may be utilized. As described above, relative proximal movement may be caused manually. Alternatively, relative proximal movement may be caused passively or caused by a combination of manual/passive action (e.g., manual trigger with passive actuation).

By way of non-limiting example, to passively achieve relative proximal movement of the hub 12 versus the body 16, a layer of pressure sensitive adhesive 42 may be provided on the distal end 30 of the body 16 configured to provide sufficient adherence to a patient's skin during an injection such that the body 16 remains relatively fixed to the patient's skin to permit proximal movement of the hub 12 relative to the body 16 with the body 16 being moved from the first position to the second position. Various pressure sensitive adhesives may be utilized with the subject invention. The layer 42 may be arranged in various patterns, including being continuous in bounding the needle 14 (e.g., such as being disc-shaped) or discontinuous in random or regular patterns.

It is noted that the layer of pressure sensitive adhesive 42 should not be excessively adherent in that the needle assembly 10 must be ultimately removed from the patient. Discomfort to the patient caused by removal of the layer 42 must be minimal. It is preferred that with the body 16 being fixedly retained by the hub 12, e.g., fixedly retained in the second position, a greater retentive force of the body 16 on the hub 12 is generated than the adherence of the layer 42 to the patient's skin S. With this arrangement, the body 16 may be removed from the patient's skin S with the body 16 maintaining a fixed position on the hub 12 and with minimal discomfort to the patient.

As indicated above, proximal movement of the hub 12 relative to the body 16 may be caused by a combination of manual and passive action. With reference to FIGS. 9-12, and by way of non-limiting example, a variation of the needle assembly 10 is shown which operates with a combination of manual (i.e., active) and passive action. In particular, a manual trigger is utilized to cause passive actuation. In this arrangement, a spring 44 is disposed between the hub 12 and the body 16 configured to urge the body 16 distally away from the hub 12. The spring 44 may be of any known type capable of generating a biasing force, including being of a coil or compression type. To provide stability to the spring 44, a secondary wall 46 may be disposed inwardly of the neck portion 22 which defines a well 48 in which the spring 44 is seated. The well 48 may be disposed between the bulkhead 20 and the neck portion 22, with the bulkhead 20 spanning the interior of the body 16 between portions of the well 48. The spring 44 is positioned to preferably act against the distal end 30 of the body 16.

One or more cam followers or protrusions 50 are preferably formed to extend inwardly from the body 16, particularly from the skirt 32. Correspondingly, one or more cam tracks 52 are formed in the hub 12, particularly at the neck portion 22. It is preferred that one track 52 be provided for each of the protrusions 50, although more than one set of the protrusions/tracks 52 may be provided. Although described as a preferred embodiment with the protrusions 50 extending from the body 16 and tracks 52 being formed in the hub 12, it will be appreciated by those skilled in the art that one or more of the protrusions 50 may be formed on the hub 12 and/or that one or more of the tracks 52 may be formed on the body 16. Reference herein shall be made to one protrusion 50 and one track 52 with the understanding that a plurality of each may be provided.

Figure 11:
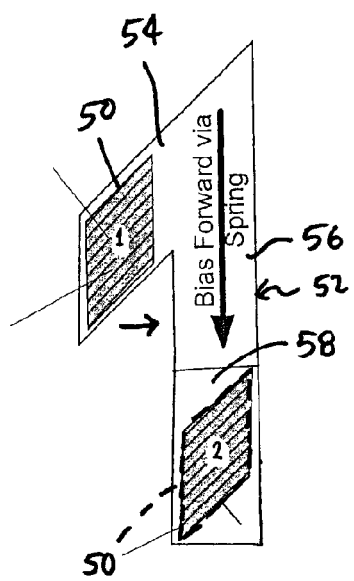
FIGS. 11 and 12 show different track arrangements useable with the subject invention.

With reference to FIG. 11, the track 52 is configured to provide at least the first and second positions described above. With reference to FIG. 11, the track 52 may have a first track portion 54 which extends generally transversely to the biasing force generated by the spring 44, represented by the arrow. A second track portion 56 communicates with, and extends from, the first track portion 54 with the second track portion 56 being generally aligned with the biasing force generated by the spring 44. The second track portion 56 is formed to extend further distally than the first track portion 54. In the first position (represented by the numeral 1 in FIG. 11), the protrusion 50 is nested within the first track portion 54. The cooperating interengagement of the protrusion 50 and the first track portion 54 resists relative axial movement between the hub 12 and the body 16 generated by the spring 44.

During use, the needle 44 is inserted into a patient to the initial depth with the body 16 being in the first position. The body 16 acts as a hard stop and limits the extent of insertion of the needle 14 into the patient. Once the needle 14 is maximally inserted, and prior to actuation of the medical injector, a predetermined extent of relative rotation between the hub 12 and the body 16 is caused so as to urge the protrusion 50 from the first track portion 54 and into the second track portion 56. Interengagement of the protrusion 50 and the track 52 limits the extent of relative rotation between the hub 12 and the body 16. Once in the second track portion 56, the spring 44 is free to urge the body 16 distally relative to the hub 12. The rotation of the protrusion 50 is a manual trigger which allows for passive relative movement between the hub 12 and the body 16 under force of the spring 44.

With interengagement of the body 16 against a patient's skin, the release of the spring 44 actually results in proximal movement of the hub 12 relative to the body 16. The extent of the relative proximal movement is limited by interengagement of the protrusion 50 against the distalmost portion of the second track portion 56. This position corresponds to the second position of the body 16, wherein drug administration may be achieved. As discussed above, the first and second positions may correspond to different depths for injection, for example, with the first position corresponding to a subcutaneous injection depth and the second position corresponding to an intradermal injection depth.

The body 16 may be caused to be fixedly retained in the second position. With reference to FIG. 11, the second track portion 56 may be provided with a recess 58 into which the protrusion 50 snap engages in the second position. The snap engagement of the protrusion 50 in the recess 58 imparts fixed retention for the body 16 relative to the hub 12.

Although it has been disclosed to use the needle assembly 10 in first and second positions, additional positions may be utilized. For example, with reference to FIG. 12, the track 52 may be provided with a third track portion 60 intermediate the first and second track portions 54, 56. The third track portion 60 may have a primary portion 62 in communication with the first track portion 54 which extends distally therefrom in a direction coinciding with the spring force generated by the spring 44. The third track portion 60 further includes a secondary portion 64 which extends transversely (transversely to the direction of the spring force of the spring 44) between the primary portion 62 and the second track portion 56. One or more retaining elements 66 may be disposed along the secondary portion 64 to catch and releasably retain the protrusion 50. Thus, during use, the protrusion 50 is initially in the first position (represented by the numeral 1) in the first track portion 54. The protrusion 50 is manually urged by relative rotation between the hub 12 and the body 16 from the first track portion 54 and into the primary portion 62 of the third track portion 60. Once in the primary portion 62, the spring 44 causes displacement of the protrusion 50 to the second position represented by the numeral 2A. The one or more retaining elements 66 maintain the protrusion 50 in the second position and restrain the protrusion 50 from further distal advancement. The restrained position may be at or in proximity to the second position and is represented by the numeral 2B. Further relative proximal movement of the hub 12 relative to the body 16 may be achieved by further causing relative rotation between the hub 12 and the body 16 with the protrusion 50 being urged past the one or more retaining elements 66 and into the second track portion 56. The spring 44 causes displacement of the protrusion 50 along the second track portion 56. The protrusion 50 may be urged to the third position, coinciding with the distalmost position of the second track portion 56 (represented by the numeral 3), under force of the spring 44 where the protrusion 50 may come into snap engagement with the recess 58.

Figure 12:
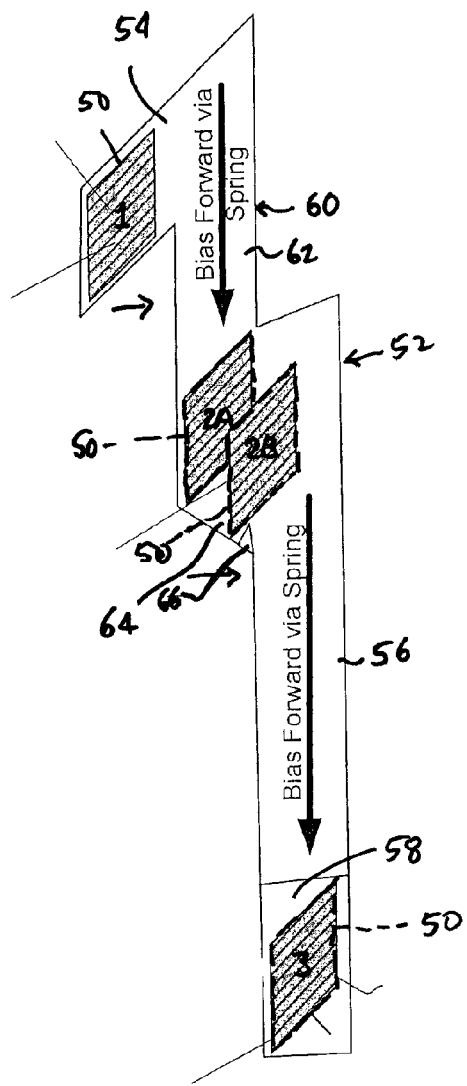

With reference to FIG. 12, the three positions of the track 52 may correspond to three different use positions: a first position (position numeral 1) corresponding to a subcutaneous depth for injection which is achieved prior to actuation of the medical injector and drug administration; a second position (position(s) numeral(s) 2A/2B) corresponding to a shallower injection depth, such as an intradermal injection depth, where drug administration is caused; and, a third position (position numeral 3) corresponding to the distal end 28 of the needle 14 being located proximally of the distal end 30 of the body 16, post drug administration. In the third position, the distal end 28 is covered by the body 16 and shielded from further contact. It is preferred that the body 16 be fixedly retained in the shielding (third) position after use. Any locking arrangement may be utilized to fixedly retain the body 16 in the third position.

As will be appreciated by those skilled in the art, various positions corresponding to various depths of injection may be provided for the needle assembly 10. The variation of the needle assembly 10 shown in FIGS. 1-8 may be formed with more than two positions, with additional retention slots being provided. For example, a third retention slot may be provided which provides for fixed retention with the distal end 28 of the needle 14 being located proximally of the distal end 30 of the body 16 in a shielded state. Manual or passive (e.g., the layer 42) action may be used to urge the body 16 to the third or any subsequent position.

What is claimed is:

1. A needle assembly comprising:
   a hub;
   a needle fixed to said hub, said needle having a proximal end and a distal end, said distal end formed for insertion into a patient; and,
   a body in engagement with said hub so as to be movable relative thereto, said body having a distal end with an aperture formed therein configured to permit passage therethrough of said needle;
   wherein, said body being releasably retainable in a first position on said hub, with said body engaging said hub, where said distal end of said needle extends distally a first distance from said distal end of said body,
   wherein, said body being retainable in a second position on said hub, with said body engaging said hub, where said distal end of said needle extends distally a second distance from said distal end of said body, said second distance being less than said first distance, and,
   wherein, said hub is displaceable proximally relative to said body to urge said body from said first position to said second position.

2. A needle assembly as in claim 1, wherein said body is fixedly retainable in said second position on said hub.

3. A needle assembly as in claim 1, wherein said body is releasably retainable in said second position on said hub.

4. A needle assembly as in claims 3, wherein, said body is fixedly retainable in a third position on said hub where said distal end of said needle is located proximally of said distal end of said body.

5. A needle assembly as in claim 4, wherein said hub is displaceable proximally relative to said body to urge said body from said second position to said third position.

6. A needle assembly comprising:
   a hub;
   a needle fixed to said hub, said needle having a proximal end and a distal end, said distal end formed for insertion into a patient;
   a body disposed on said hub so as to be movable relative thereto, said body having a distal end with an aperture formed therein configured to permit passage therethrough of said needle; and,
   a pressure sensitive adhesive disposed on said distal end of said body,
   wherein, said body being releasably retainable in a first position on said hub where said distal end of said needle extends distally a first distance from said distal end of said body,
   wherein, said body being retainable in a second position on said hub where said distal end of said needle extends distally from said distal end of said body less than said first distance from said distal end of said body, or is located proximally of said distal end of said body, and,
   wherein, said adhesive is configured to provide sufficient adherence to a patient's skin during an injection such that said body remains relatively fixed to the patient's skin with proximal movement of said hub relative to said body with said body being adjusted from said first position to said second position on said hub.

7. A needle assembly comprising:
   a hub;
   a needle fixed to said hub, said needle having a proximal end and a distal end, said distal end formed for insertion into a patient;
   a body in engagement with said hub so as to be axially and radially movable relative thereto, said body having a distal end with an aperture formed therein configured to permit passage therethrough of said needle;
   a spring element for urging said body distally away from said hub; and,
   a cooperatively coupled cam track having at least a first position and a second position and cam follower wherein the cam track is disposed either on the body or the hub and the cooperating cam follower is disposed on the opposing part, thereby constraining relative axial motion between said hub and body,
   wherein, said body being releasably retainable in a first position where said relative axial distal end of said needle extends distally a first distance from said distal end of said body,
   wherein, said body being retainable in a second position on said hub where said distal end of said needle extends distally from said distal end of said body less than said first distance from said distal end of said body, or is located proximally of said distal end of said body, and,
   wherein, said cam track and said cam follower cooperate during an injection procedure to permit distal axial movement of said body, biased by said spring, with said body being moved from said first position to said second position after a predetermined extent of radial motion between said body and said hub.

8. A needle assembly as in claim 7, wherein said body is fixedly retainable in said second position on said hub.

9. A needle assembly as in claim 7, wherein said body is retained in said second position on said hub by a detent in said cam track.

10. A needle assembly as in claim 7, wherein, said cam track has a third position and said body is fixedly retainable in said third position where said distal end of said needle is located proximally of said distal end of said body.

* * * * *